(12) United States Patent
Sepetka et al.

(10) Patent No.: US 6,849,081 B2
(45) Date of Patent: Feb. 1, 2005

(54) IMPLANT DELIVERY ASSEMBLY WITH EXPANDABLE COUPLING/DECOUPLING MECHANISM

(75) Inventors: Ivan Sepetka, Los Altos, CA (US); U. Hiram Chee, San Carlos, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/730,215

(22) Filed: Dec. 5, 2000

(65) Prior Publication Data

US 2001/0002438 A1 May 31, 2001

Related U.S. Application Data

(63) Continuation of application No. 09/034,606, filed on Mar. 3, 1998, now Pat. No. 6,238,415, which is a continuation of application No. 08/363,264, filed on Dec. 22, 1994, now Pat. No. 5,814,062.

(51) Int. Cl.$^7$ .............................................. A61B 17/08
(52) U.S. Cl. .......................................... 606/213; 606/1
(58) Field of Search ........................... 606/1, 108, 151, 606/190–200, 213, 158, 159; 623/1.1, 1.11, 1.22, 11.11; 128/207.14–207.18; 604/96.01–96.109; 600/201, 204, 207, 210

(56) References Cited

U.S. PATENT DOCUMENTS

| | | | |
|---|---|---|---|
| 3,773,034 A | 11/1973 | Burns et al. | |
| 3,952,747 A | 4/1976 | Kimmel, Jr. | |
| 4,311,146 A | * 1/1982 | Wonder | 604/96.01 |
| 4,327,734 A | 5/1982 | White, Jr. | |
| 4,341,218 A | 7/1982 | Ü | |
| 4,597,389 A | 7/1986 | Ibrahim et al. | |
| 4,739,768 A | 4/1988 | Engelson | |
| 4,787,899 A | 11/1988 | Lazarus | |
| 4,813,934 A | 3/1989 | Engelson et al. | |
| 4,884,579 A | 12/1989 | Engelson | |
| 4,969,458 A | 11/1990 | Wiktor | |
| 4,994,069 A | 2/1991 | Ritchart et al. | |
| 5,002,556 A | 3/1991 | Ishida et al. | |
| 5,011,482 A | 4/1991 | Goode et al. | |
| 5,055,101 A | 10/1991 | McCoy | |
| 5,108,407 A | 4/1992 | Geremia et al. | |
| 5,122,136 A | 6/1992 | Guglielmi et al. | |
| 5,143,085 A | 9/1992 | Wilson | |
| 5,167,624 A | 12/1992 | Butler et al. | |
| 5,217,484 A | * 6/1993 | Marks | 606/200 |
| 5,234,437 A | 8/1993 | Sepetka | |
| 5,250,071 A | 10/1993 | Palermo | |
| 5,261,916 A | 11/1993 | Engelson | |
| 5,312,415 A | 5/1994 | Palermo | |
| 5,345,927 A | 9/1994 | Bonutti | |
| 5,354,295 A | 10/1994 | Guglielmi et al. | |
| 5,522,836 A | 6/1996 | Palermo | |
| 5,634,928 A | * 6/1997 | Fischell et al. | 623/1.11 |

(List continued on next page.)

FOREIGN PATENT DOCUMENTS

| | | |
|---|---|---|
| EP | 0 375 775 A | 7/1990 |
| EP | 0442657 | 8/1991 |
| FR | 2580504 | 10/1986 |
| FR | 2645028 | 10/1990 |

(List continued on next page.)

Primary Examiner—Glenn K. Dawson
(74) Attorney, Agent, or Firm—Bingham McCutchen LLP

(57) ABSTRACT

An occlusive implant delivery assembly includes a rapid response decoupling or detachment mechanism that does not effect significant migration of the implant during release. The assembly includes an occlusive implant device, such as an embolic coil, a pusher or device to carry the implant to the selected location, and an expandable coupling-decoupling mechanism for releasing the implant at the selected site. The mechanical construction provides rapid release times. In addition, the releasing mechanism generally operates without exerting any significant force on the implant, thereby avoiding any significant displacement of the implant during release.

16 Claims, 6 Drawing Sheets

U.S. PATENT DOCUMENTS

| | | | | |
|---|---|---|---|---|
| 5,669,931 A | * | 9/1997 | Kupiecki et al. | 606/191 |
| 5,690,666 A | * | 11/1997 | Berenstein et al. | 606/191 |
| 5,733,294 A | | 3/1998 | Forber et al. | |
| 5,743,905 A | | 4/1998 | Eder et al. | |
| 5,800,454 A | | 9/1998 | Jacobsen et al. | |
| 5,814,062 A | * | 9/1998 | Sepetka et al. | 606/198 |
| 5,855,578 A | | 1/1999 | Guglielmi et al. | |
| 5,891,128 A | | 4/1999 | Gia et al. | |
| 5,891,130 A | | 4/1999 | Palermo et al. | |
| 5,891,155 A | | 4/1999 | Irie | |
| 5,895,385 A | | 4/1999 | Guglielmi et al. | |
| 5,895,391 A | | 4/1999 | Farnholtz | |
| 5,911,717 A | | 6/1999 | Jacobsen et al. | |
| 5,916,235 A | | 6/1999 | Guglielmi | |
| 5,919,187 A | | 7/1999 | Guglielmi et al. | |
| 5,925,037 A | | 7/1999 | Guglielmi et al. | |
| 5,925,062 A | | 7/1999 | Purdy | |
| 5,928,226 A | | 7/1999 | Guglielmi et al. | |
| 5,944,714 A | | 8/1999 | Guglielmi et al. | |
| 5,944,733 A | | 8/1999 | Engleson | |
| 6,063,100 A | * | 5/2000 | Diaz et al. | 606/191 |
| 6,183,491 B1 | * | 2/2001 | Lulo | 606/191 |
| 6,254,612 B1 | * | 7/2001 | Hieshima | 606/108 |

FOREIGN PATENT DOCUMENTS

| | | |
|---|---|---|
| FR | 2 696 636 | 4/1994 |
| GB | 2245495 | 1/1992 |
| JP | 63-139565 | 6/1988 |
| JP | 06-246004 | 9/1994 |
| JP | 07-155331 | 6/1995 |
| WO | WO 92/14408 | 9/1992 |
| WO | WO 92/21400 | 12/1992 |
| WO | WO 94/06503 | 3/1994 |
| WO | WO 97/48351 | 12/1997 |
| WO | WO 98/02100 | 1/1998 |
| WO | WO 98/04198 | 2/1998 |
| WO | WO 98/04315 | 2/1998 |

* cited by examiner

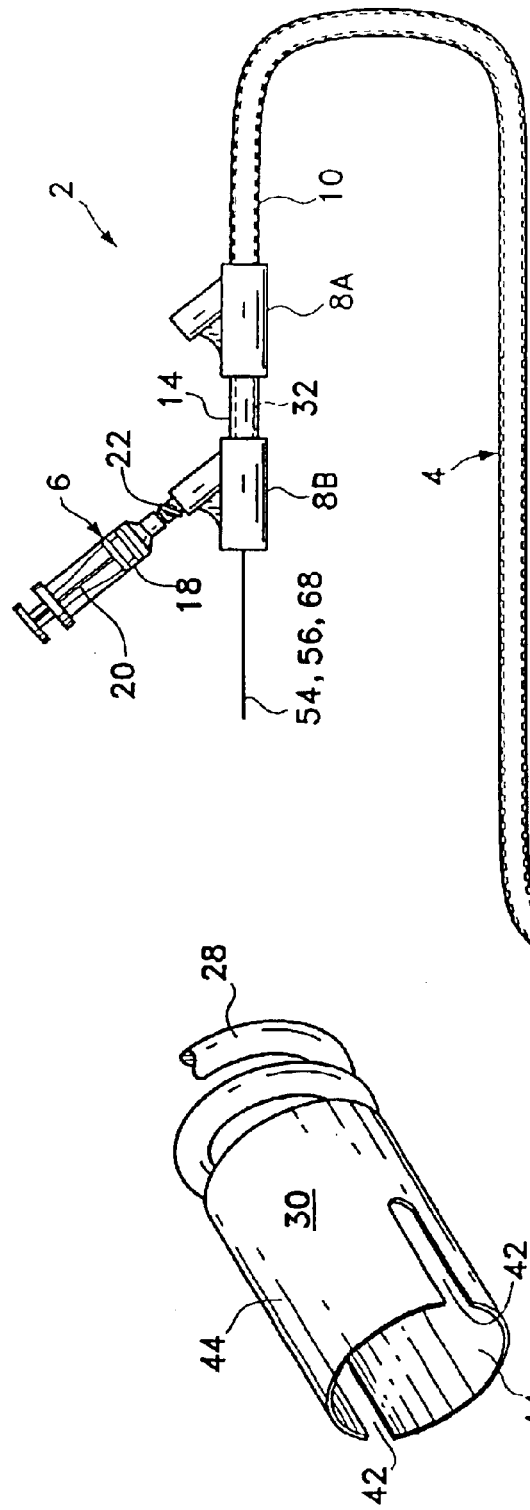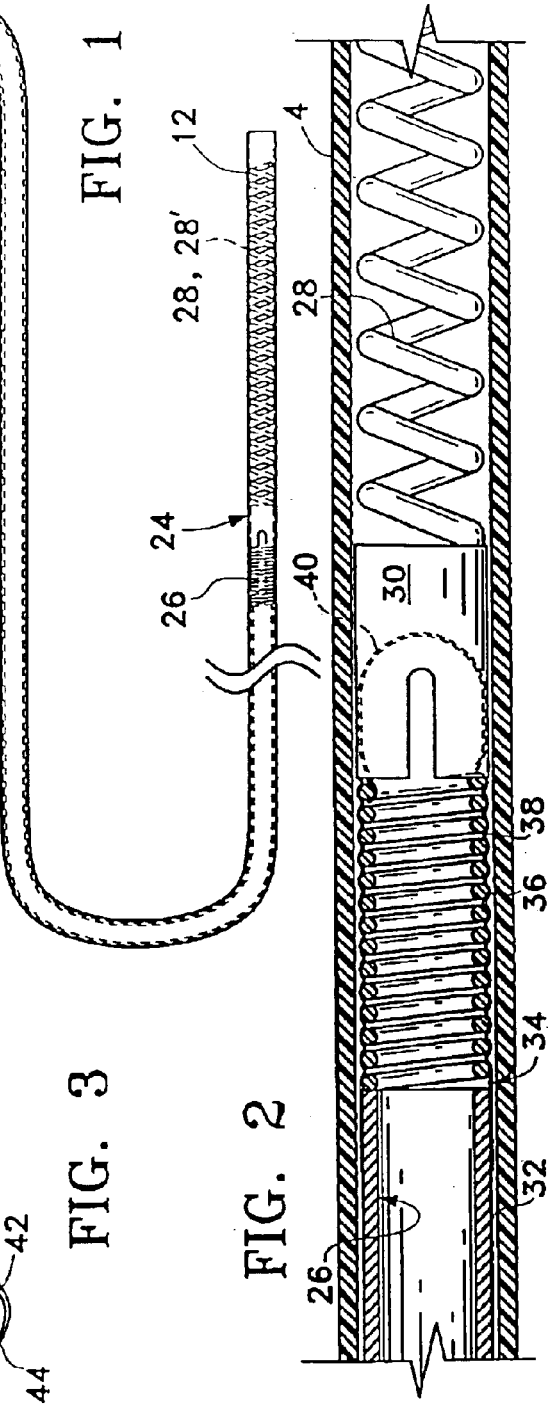

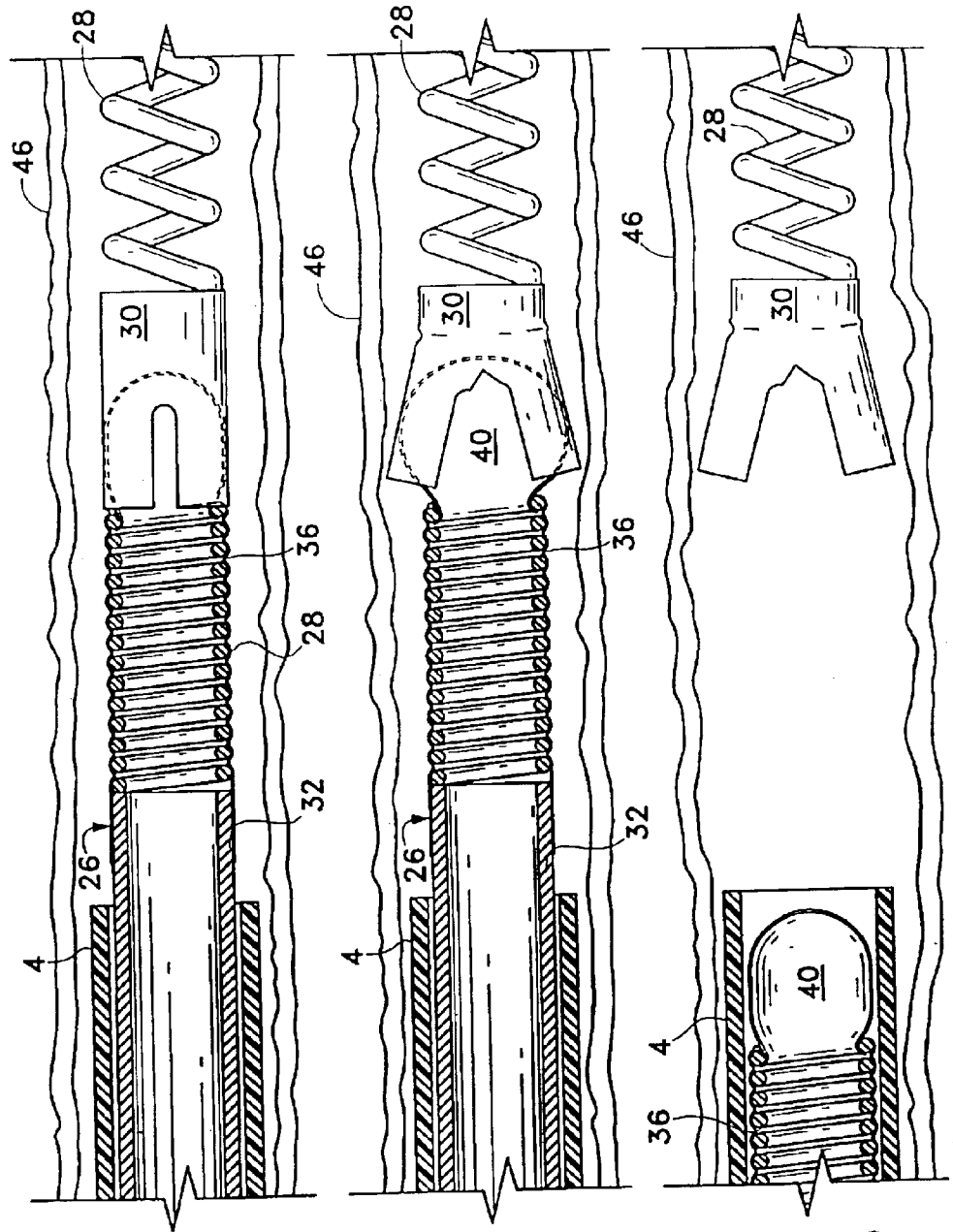

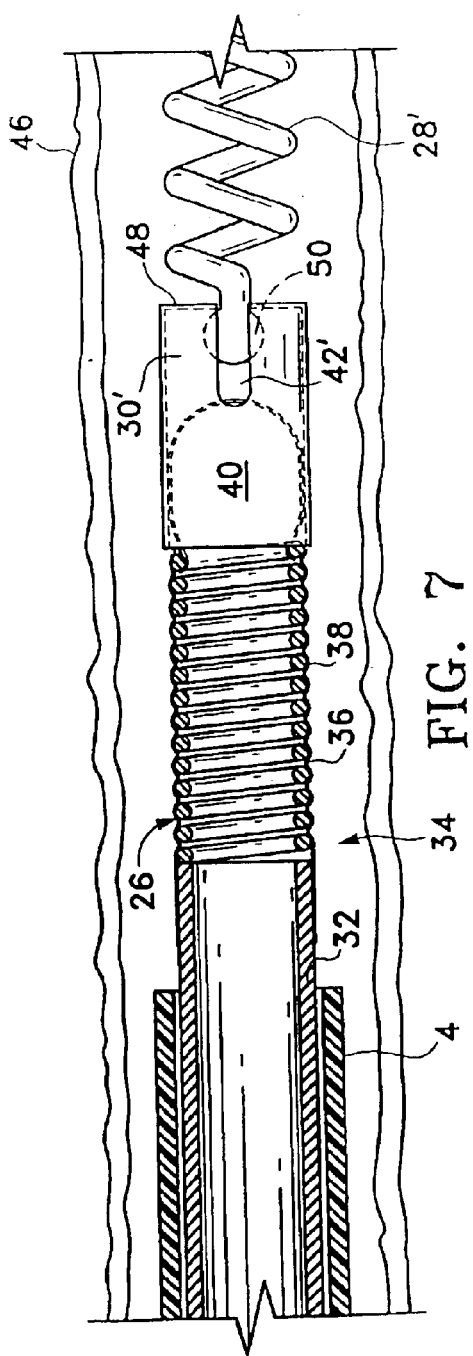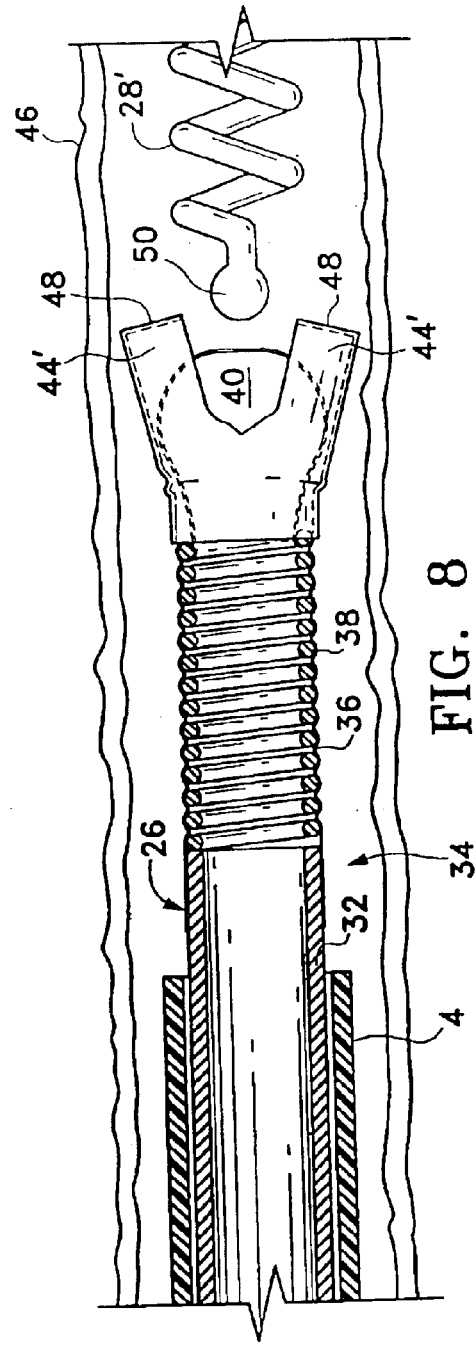

IMPLANT DELIVERY ASSEMBLY WITH EXPANDABLE COUPLING/DECOUPLING MECHANISM

RELATED PATENT APPLICATION

This application is a continuation of U.S. patent application Ser. No. 09/034,606, now U.S. Pat. No. 6,238,415, filed on Mar. 3, 1998, which is a continuation of U.S. patent application Ser. No. 08/363,264, now U.S. Pat. No. 5,814,062, filed on Dec. 22, 1994.

FIELD OF THE INVENTION

The present invention generally relates to surgical instruments. More particularly, the invention relates to delivery assemblies for delivering an occlusive device, such as an embolic coil, to a selected site within a mammal using an expandable coupling or decoupling mechanism.

BACKGROUND OF THE INVENTION

The endovascular treatment of a variety of vascular maladies throughout the body is an increasingly more important form of therapy. Catheters have been used to place various treatment materials, devices, and drugs within arteries and veins in the human body. Examples of these devices and their use in such treatments are shown in U.S. Pat. Nos. 5,234,437 and 5,261,916, in which methods and devices for delivery of coils or wires within the human body to sites, such as aneurysms, to occlude those sites are disclosed. Coils, such as those discussed in these documents as well as in U.S. Pat. No. 4,994,069, may be of a regular or helical configuration or assume a random convoluted configuration at the site. The coils normally are made of a radiopaque, biocompatible metal such as platinum, gold, tungsten or alloys of these and other metals. In treating aneurysms, it is common to place a number of coils within the aneurysm. The coils occlude the site by posing a physical barrier to blood flow and by promoting thrombus formation at the site.

Coils have typically been placed at the desired site within the vasculature using a catheter and a pusher. The site is first accessed by the catheter. In treating peripheral or neural conditions requiring occlusion, the sites are accessed with flexible, small diameter catheters such as those shown in U.S. Pat. Nos. 4,739,768 and 4,813,934. The catheter may be guided to the site through the use of guidewires (see U.S. Pat. No. 4,884,579) or by flow-directed means such as balloons placed at the distal end of the catheter. Use of guidewires involves the placement of relatively long, torqueable proximal wire sections within the catheter attached to more flexible distal end wire sections designed to be advanced across sharp bends at vessel junctions. The guidewire is visible using x-ray techniques and allows a catheter to be navigated through extremely tortuous vessels, even those surrounded by soft tissue such as the brain.

Once the site has been reached, the catheter lumen is cleared by removing the guidewire (if a guidewire has been used), and one or more coils are placed into the proximal open end of the catheter and advanced through the catheter with a pusher. Pushers are wires having distal ends adapted to engage and push the coil through the catheter lumen as a pusher itself is advanced through the catheter. Once the coil reaches the distal end of the catheter, it is discharged from the catheter into the pusher into the vascular site. However, there are concerns when discharging the coil from the distal end of the catheter. For example, the plunging action of the pusher and the coil can make it difficult to position the coil at the site in a controlled manner and with a fine degree of accuracy. Inaccurate placement of the coil can be problematic because once the coil has left the catheter, it is difficult to reposition or retrieve the coil.

Several techniques involving Interlocking Detachable Coils (IDCs), which incorporate mechanical release mechanisms and Guglielmi Detachable Coils (GDCs), which utilize electrolytically actuated release mechanisms, have been developed to enable more accurate placement of coils within a vessel.

One technique for detaching an embolic coil is shown in U.S. Pat. No. 5,261,916. According to that technique, a coil having an enlarged portion is mated with a pusher having a keyway adapted to receive the enlarged portion of the coil in an interlocking relationship. The joint between the pusher and the coil is covered by a coaxial member. The coaxial member is movable by sliding the member axially. As the coaxial member is moved away from the junction where the coil's member engages the keyway of the pusher, the coil is freed from the catheter assembly and the pusher may then be removed.

Another IDC device for placement of coils is shown in U.S. Pat. No. 5,234,437. This device includes a coil having a helical portion at least one end and a pusher wire having a distal end that is threaded inside on the helical coil by use of a threaded section on the outside of the pusher. The device operates by engaging the proximal end of the coil with a sleeve and unthreading the pusher from the coil. Once the pusher is free, the sleeve may be used to push the coil out into the targeted treatment area.

U.S. Pat. No. 5,312,415 discloses the use of a catheter having a constricted or feathered end to retain a number of embolic coils on a guidewire for precise placement using a pusher sheath.

Electrolytic coil detachment is disclosed in U.S. Pat. Nos. 5,122,136 and 5,354,295. As disclosed in U.S. Pat. No. 5,122,136, the coil is bonded via a metal-to-metal joint to the distal end of the pusher. The pusher and coil are made of dissimilar metals. The coil-carrying pusher is advanced through the catheter to the site and a small electrical current is passed through the pusher-coil assembly. The current causes the joint between the pusher and the coil to be severed via electrolysis. The pusher may then be retracted leaving the detached coil at an exact position within the vessel. Since no significant mechanical force is applied to the coil during electrolytic detachment, highly accurate coil placement is readily achieved. In addition, the electric current may facilitate thrombus formation at the coil site. The only perceived disadvantage of this method is that the electrolytic release of the coil may require a period of time that may inhibit rapid detachment of the coil from the pusher.

Another method of placing an embolic coil is disclosed in U.S. Pat. No. 5,108,407. This patent shows the use of a device in which embolic coils are separated from the distal end of a catheter by the use of heat-releasable adhesive bonds. The coil adheres to the therapeutic device via a mounting connection having a heat sensitive adhesive. Laser energy is transferred through a fiber optic cable which terminates at that connector. The connector becomes warm and releases the adhesive bond between the connector and the coil. Among the drawbacks of this system is that it involves generally complicated laser optic componentry.

There is a need to provide alternative mechanical mechanisms for delivering implants, such as embolic coils, that combine accurate positioning capability with rapid implant decoupling response times.

SUMMARY OF THE INVENTION

The present invention provides a mechanical occlusive implant delivery assembly having a rapid response decoupling or detachment mechanism that does not effect significant migration of the implant during release. The assembly includes an occlusive implant device, such as an embolic coil, a pusher or device to carry the implant to the selected location, and an expandable mechanism that is expanded or contracted to release the implant at the selected site. The invention advantageously incorporates a release mechanism that simply involves unloading a locking force, which is preferably uniformly applied, thereby avoiding the transmission of any significant force to the implant during release. In addition, the locking members preferably have generally, smooth, rounded configurations so that they do not catch and dislodge previously positioned coils upon retraction.

According to a first embodiment of the invention, the occlusive implant delivery assembly includes an occlusive implant; a pusher having a proximal section and a distal section; a coupling having first and second portions, the first portion being coupled to the distal section of the pusher and the second portion being coupled to the implant; and an inflatable member having a proximal portion and a distal portion, the proximal portion being coupled to the distal section of the pusher. At least a portion of the inflatable member is disposed in the coupling such that when inflated, it expands the coupling and decouples the coupling from either the implant or the pusher. With this arrangement, rapid implant release times can be achieved with minimal, if any, force being applied to the implant. That is, the hydraulic pressure is only transmitted to the detachment point or juncture between the inflatable member and the implant, and not to the implant.

According to another aspect of this embodiment, the inflatable member and coupling are configured so that the hydraulic pressure generated by the inflatable member is applied uniformly to the inner circumferential surface of the coupling. Thus, any force that may be applied to the implant in the radial direction is countered by an equal, but opposite force, thereby avoiding implant displacement during release. In the preferred embodiment, the coupling is cylindrical with an essentially uniform radius and the inflatable member is essentially symmetrical about its longitudinal axis in the inflated and uninflated states.

According to another embodiment of the invention the implant delivery assembly comprises an occlusive implant having a tubular portion; a pusher having a proximal section and a distal section; and an inflatable member having a first portion coupled to the distal section of the pusher and a second portion disposed in the tubular portion of the implant such that upon inflation of the inflatable member the implant and member tend to separate. More specifically, the coil slides off of the inflatable member. In addition to causing minimal post delivery migration of the implant, this construction provides an advantageously simple one-piece decoupling mechanism, which can be readily manufactured.

According to another aspect of this embodiment, the inflatable member and tubular portion also are configured as described above so that the hydraulic pressure generated by the inflatable member is applied uniformly to the inner circumferential surface of the tubular portion. In the preferred embodiment, the inner surface of the tubular portion is essentially symmetrical about its longitudinal axis and the inflatable member is essentially symmetrical about its longitudinal axis when inflated or deflated to provide an essentially uniformly distributed force to the inner circumference of the tubular section.

According to yet a further embodiment of the invention, the implant delivery assembly comprises an occlusive implant having a tubular portion; a pusher having a proximal section and a distal section; a core member slidably disposed within the pusher and extending into the tubular portion; and a locking member releasably coupled to the coil and core member. With this construction the release mechanism is simply mechanically expanded to interlock the implant to the pusher and relaxed to release the implant.

In a first configuration, the locking member comprises an elastomeric ring, such as an O-ring, and the core member includes a locking portion and a tapered portion adjacent thereto. The diameter of the core member exceeds the inner diameter of the ring such that when the ring is positioned on the locking portion it expands and frictionally locks the tubular portion thereto. On the other hand, the tapered portion tapers to a diameter that allows the ring to contract. In the preferred embodiment, the tapered portion is less than or equal to the inner diameter of the ring when the ring is in its relaxed state. When the core member is retracted, the tapered portion becomes positioned within the ring and allows the ring to radially contract and release the tubular portion and, thus, the implant, as the locking member returns to its relaxed state.

In another configuration, the locking member comprises a flexible sleeve and the core member extends into the sleeve and is secured thereto. The sleeve is configured so that when axially compressed, it expands radially against the inner surface of the tubular portion and frictionally locks the implant thereto. The core member is retracted to compress the sleeve against a restraint, expand it radially and lock the implant to the delivery assembly. When it is desired to release the implant, the core member is advanced to remove the axial compression and radially contract the sleeve.

These configurations advantageously eliminate the need for auxiliary hydraulics.

The above is a brief description of some of the features and advantages of the present invention. Other features, advantages and embodiments of the invention will be apparent to those skilled in the art from the following description, accompanying drawings and appended claims.

BRIEF DESCRIPTION OF THE DRAWINGS

FIG. 1 shows a catheter apparatus constructed according to a general embodiment of the present invention;

FIG. 2 is an enlarged, fragmentary view of an occlusive implant delivery assembly, constructed according to the principles of the present invention, disposed within a catheter;

FIG. 3 is a perspective view of the coupling mechanism that forms part of the release mechanism shown in FIG. 2;

FIG. 4 is an enlarged, fragmentary view of the implant delivery assembly of FIG. 2 with the implant positioned at a desired location;

FIG. 5 is a further view of the implant delivery assembly shown in FIG. 4 with the coupling of the release mechanism expanded to unlock and release the implant from the pusher;

FIG. 6 shows the release mechanism deflated and retracted from the implant location;

FIG. 7 is an enlarged, fragmentary view of another embodiment of the implant delivery system of the present invention with the release mechanism in a locked state;

FIG. 8 illustrates the release mechanism of FIG. 7 in an unlocked state;

DETAILED DESCRIPTION OF THE PREFERRED EMBODIMENTS

Figure 9:
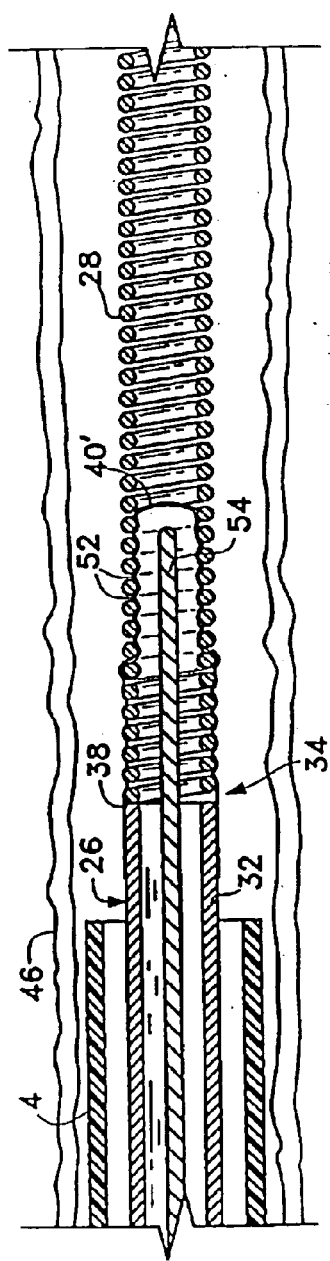
FIG. 9 is a further embodiment of the release mechanism of the present invention.

Referring to the drawings in detail, wherein like numerals indicate like elements, several embodiments of an occlusive implant delivery assembly are shown according to the principles of the present invention. The various embodiments employ an expandable mechanism, which is expanded or contracted, to decouple and release the implant at the desired site. Although variously configured implants can be used in conjunction with the assembly of the present invention, an embolic coil type implant will be described for purposes of example.

The operation of the assembly generally comprises the steps of (1) advancing a catheter through a vessel lumen, for example, to the vicinity of the site to be occluded (e.g., an aneurysm, vascular malformation, or arterial venous fistula), (2) advancing the implant delivery assembly through and beyond the catheter to the location, and (3) radially expanding or contracting the release mechanism to detach the implant from the assembly.

Referring to FIG. 1, a catheter apparatus 2 suitable for guiding the occlusive implant delivery assembly and providing actuation pressure for the hydraulically actuated release mechanism embodiments is shown. Catheter apparatus 2 generally includes a catheter 4, syringe 6 and sidearms (adapters) 8A and 8B. Catheter 4 generally comprises an elongate tubular member having proximal and distal end portions 10 and 12. The catheter is preferably between about 50–300 cm in length, and typically between about 60–200 cm in length. The catheter also is designed for accessing a vessel site at which, for example, vasoocclusion is desired. For example, the vessel site may be within a small diameter vessel having 2–5 mm lumen diameter and accessible by way of a tortuous vessel path which may involve sharp vessel turns and multiple vessel branches. In that case, the catheter preferably has a small diameter, flexible construction with a lumen diameter of less than about 40 mil, and preferably between about 8–30 mil. Catheters of this type, which are typically used for accessing deep brain vascular sites, are commercially available.

The elongated tubular member or catheter 4 is secured at its proximal end 10 to sidearm 8A, which is of conventional design for introducing fluids or apparatus into the catheter. The end of proximal section 32 of pusher 26, which will be described in more detail below, extends through sidearm 8A and is coupled to the distal or downstream end of sidearm 8B. Sidearm 8B, which is otherwise essentially similar in construction to sidearm 8A, can include a tubular extension 14 that surrounds a portion of the pusher as shown in FIG. 1. Mandrel 54, 56 or 68, which extends through the pusher, as will be discussed below in connection with FIGS. 9–15, extends through one tube of sidearm 8B. The discharge tip of syringe 6, which is used in conjunction with the embodiments shown in FIGS. 2–11 is fluidly coupled to the other tube of sidearm 8B and, thus, the inner lumen of pusher 26 through which the aforementioned mandrels extend.

Syringe 6 is of conventional construction and includes a cylindrical barrel 18 and a plunger 20 that is reciprocally mounted therein. A stopcock 22 preferably is provided in the discharge piece of the syringe for opening or closing the fluid connection between the syringe and pusher lumen. Alternatively, the stopcock can be provided in a connector (not shown) that couples the discharge piece of the syringe to sidearm 8B. When the stopcock is in the closed position, the decoupling or release mechanism of the implant delivery assembly will not be inadvertently actuated, thereby avoiding wrongly positioning the implant within the body as a result of such accidental discharge of liquid from the syringe into the catheter.

As discussed above, the implant delivery assembly, which is generally designated with reference numeral 24 in FIG. 1, is guided through catheter 4 towards the intended vasoocclusion site. Occlusive implant delivery assembly 24 generally comprises a pusher or elongated carrier member 26, a coil type occlusive implant 28 and a decoupling or release mechanism for releasing the implant from the assembly. Although coil 28 is shown in the drawings as a uniform diameter helical coil wire, it may have other configurations. It is important, however, that the coil be dimensioned to be able to be advanced through a catheter that is sized to access the desired site. The coil may be made of radiopaque, biocompatible metal such as platinum, gold, tungsten, stainless steel or alloys of these metals. Preferably, the coil comprises platinum, gold, tungsten or alloys of these metals so that its location at the site may be readily viewed radiographically.

For use in occluding peripheral or neural sites, the coils will typically be made of 0.05 to 0.15 mm diameter platinum wire that is wound to have an inner diameter of 0.15 to 0.96 mm with a minimum pitch (i.e., the windings are close or tight). The length of the wound wire (i.e., the coil) will normally be in the range of 0.5 to 60 cm, and preferably 0.5 to 40 cm. For wires intended for use in vessels with diameters of about 2 mm and smaller, the coil has a preferred length of about 0.5 to 20 cm. The coil can have any shape. For example, it can be formed so that it takes an essentially linear configuration in which it may be advanced through the catheter and assume a randomly oriented configuration, such as helical, after it is released from the catheter and in a relaxed state as disclosed in U.S. Pat. No. 4,994,069, which is hereby incorporated herein by reference.

Referring to FIGS. 2–6, a first embodiment of the occlusive implant delivery assembly, will be described. The delivery assembly shown in FIGS. 2–6 generally comprises a pusher or elongated carrier member 26, coil 28 and coupling 30. The pusher preferably has a tubular construction to provide a lumen for fluidly coupling a source of pressurized fluid, such as syringe 6, and an inflatable member utilized in decoupling the coil from the pusher, as will be described in more detail below. Pusher 26 also preferably has a proximal section that is rigid enough to facilitate torque transmission to the distal portion of the pusher. The distal section of the pusher may be constructed to be more flexible than the proximal portion to facilitate navigation of the distal section into very tiny vessels encountered in the brain, for example.

In the preferred embodiment, proximal tubular section of pusher 26 (designated with reference numeral 32) is a metal tube, preferably a stainless steel tube, and the distal section of pusher 26, section 34, comprises a coil 36, which is wrapped in a flexible, elastomeric film 38 to fluidly seal the spaces between the coil windings. Film 38 also overlaps section 34 to seal the juncture between section 34 an coil 36. Film 38 can be in the form of shrinkwrap and, thus, applied to coil 36 and proximal section 34 with conventional shrink-wrap techniques. Coil 36 and, thus, distal coiled section 34 is secured to the proximal tubular section 32 by welding, soldering, brazing, or adhesive.

Alternatively, a more simple pusher configuration may be used in which the pusher comprises a rigid plastic tube which can be ground with a tapered distal section to achieve the desired flexibility. Suitable materials for this configuration include PEEK and polyimide. The inner diameter of the distal section in this configuration preferably is significantly less than the outer diameter of the proximal section to which the balloon can attached (e.g., glued). In a preferred embodiment, the lumen, which provides for fluid flow between the source of pressurized fluid and the balloon, has a diameter of about 0.007 inch throughout its length and the distal section has an outer diameter of about 0.014 inch. The outer diameter of the proximal section depends on the application. For a 3 French catheter, the outer diameter of the proximal section may be about 0.016 to 0.018 inch. Although particular pusher configurations have been described, it should be understood that other configurations may be used without departing from the scope of the invention.

A conventional inflatable balloon 40, having a construction similar to those used in conventional balloon catheters, is secured to the distal end of coil 36 by adhesive, for example, such that a fluid tight path is formed between the interior of the balloon and the central lumen of pusher 26, which is formed by proximal and distal sections 32, 34 of pusher 26.

Returning to FIG. 2, balloon 40 extends into tube 42, which is also secured to implant coil 28 by welding, soldering, brazing or adhesive. As shown in FIG. 2, coupling 30 comprises a tubular member or split tube having slots formed in the axial direction and which open into the end of the tube that is directly coupled to the distal portion of pusher coil 38. The tube to pusher coupling can be accomplished by a pressure fit, welding, soldering, brazing or adhesive. Slots 42 form multiple segments 44 in tubular coupling 30 and facilitate displacement of those segments to effect release of the coil implant from the pusher, as will be described in more detail below. Although a two slot configuration is shown, other multiples of slots can be used to facilitate displacement of the proximal portion of the coupling as well as other conventional jaw or latch clamping configurations.

Tubular coupling 30 can be made from platinum, stainless steel or plastic that is biocompatible with the environment in which the coupling will be placed. The coupling 30 preferably also has a very thin wall of about 0.001 to 0.0003 inches.

The implant delivery assembly of FIGS. 2–6 will be further described by way of the following operative example which is provided merely for exemplary purposes and is not intended to limit the invention to a particular application.

A catheter is inserted through the vessel lumen to the site to be occluded (e.g., an aneurysm, vascular malformation, or arteriovenous fistula. Conventional catheter insertion and navigational procedures involving guidewire and/or flow-directed means may be used to access the site with the catheter. Thus, although not shown, catheter 4 may include a guidewire useable therewith to guide the distal end of the catheter toward the desired or selected occlusion site. Guidewires of this type are commercially available, and generally include an elongate wire having a tapered, wire-wound distal end region which is adapted to be advanced through a tortuous vessel path, with the catheter being moved axially along the advanced guidewire.

Once the distal end of the catheter is positioned at the selected site (its location may be determined by a coating at the distal end of the catheter with a radiopaque material or otherwise affixing such a material to the distal end of the catheter or incorporating such a material into the distal end of the catheter), the catheter is cleared. For example, if a guidewire has been used to position the catheter, it is withdrawn from within the catheter.

Then, the implant delivery assembly, as shown in FIG. 2, is introduced into the proximal end portion of catheter 4, and advanced toward the distal end portion of catheter 4. The proximal end of pusher 26 is manipulated via sidearm 8B, to which it is attached, so that coupling 30 and coil implant 28 extend beyond the distal end of the catheter with coupling 30 free of the catheter and the coil positioned exactly at the desired site (FIG. 4). Stopcock 22 is then placed in an open position and the plunger of syringe 6 advanced to inflate balloon 40 as shown in FIG. 5. As balloon 40 is inflated, it further opens split tube or coupling 30, i.e., segments 44 are displaced radially outward to decouple coupling 30 and coil 28 from pusher 26 without transmitting any significant force to coil 28. The balloon is then deflated by retracting the plunger in syringe 6, thereby releasing coupling 30 from balloon 40 so that the pusher can be retracted without altering the position of coil 28. After the desired number of coils have been placed at the site, the catheter is withdrawn from the vessel.

Referring to FIGS. 7 and 8, a further embodiment of the release or decoupling mechanism is shown similar to that shown in FIGS. 2–6, but in which coupling 30' has its proximal portion fixedly secured to the distal end of coiled portion 34. In addition, coupling 30' includes end walls 48 at its distal end for overlapping end piece or cap 50 provided at the proximal end of coil implant 28'. That is the end walls, which generally form jaws, releasably secure coil 28' to coupling 30' and, thus, releasably secure coil 28' to pusher 26. Coupling 30' also differs from coupling 30 in that slots 42' are formed in the distal portion of the coupling. Once the coil implant is positioned at the desired location, fluid is introduced through the hollow pusher member and into balloon 40, as described above, to displace segments 44' radially outward and release coil 28' from coupling 30' (FIG. 8). The balloon can then be deflated and the pusher retracted. With this configuration, the coupling is advantageously withdrawn with the pusher.

Figure 10:
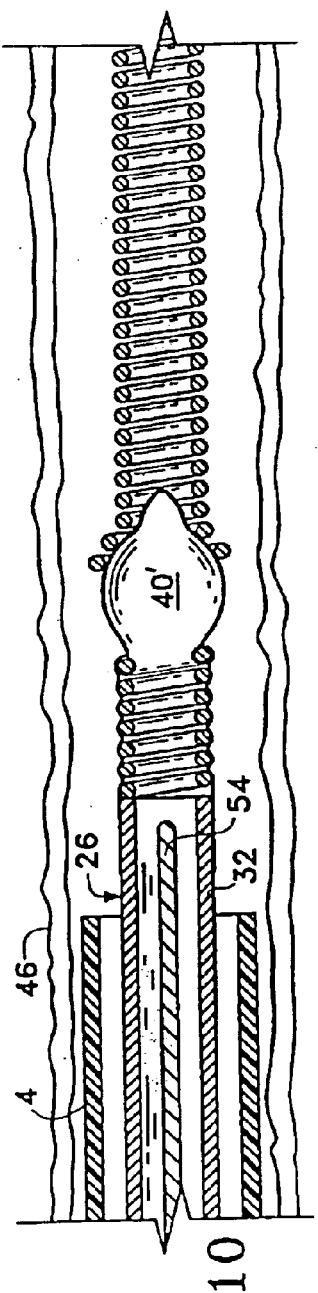
FIG. 10 is a further view of the release mechanism shown in FIG. 9 showing the mechanism actuated to release the coil therefrom.
Figure 11:
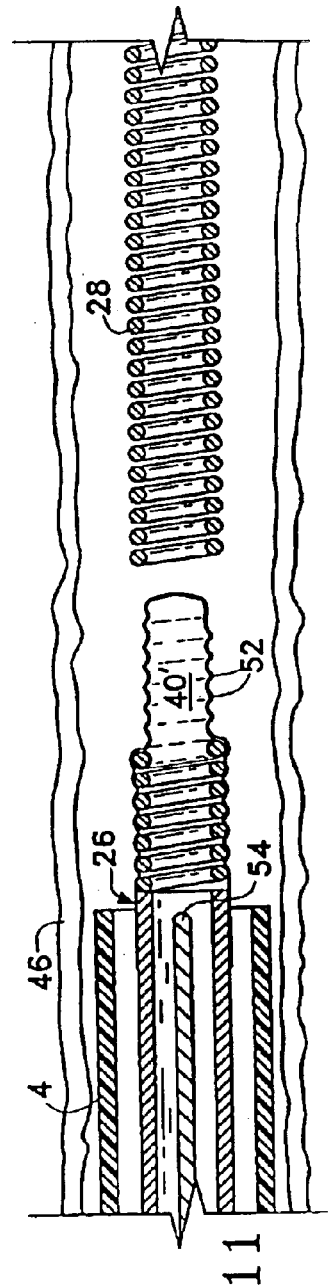
FIG. 11 is a further view of the release mechanism shown in FIGS. 8 and 9 illustrating the implant fully detached from the mechanism.

Referring to FIGS. 9–11, a further embodiment of the invention is shown. This embodiment essentially differs from those described above in that the release or decoupling mechanism simply comprises a balloon. The balloon extends from the pusher with its proximal portion close fit within coil 28. When it is desired to deploy the coil, the balloon is inflated, and as the balloon expands, the coil slides off the end of the balloon as will be described in more detail below.

The decoupling mechanism of FIGS. 9–11 comprises a balloon 40' having its open end secured to the distal coiled section 34 of pusher 26, for example, by adhesive. Balloon 40' is packed into the proximal portion of coil 28 such that the balloon frictionally engages the inner surface of coil 28 and secures the coil to the balloon. To enhance the securement between the coil and balloon, the balloon is constructed such that, when in the deflated state, the balloon has a plurality of circumferentially extending ribs 52, which preferably are configured to have a pitch corresponding to that of the coil so that the ribs can snugly fit between the windings of the coil. The ribs can be formed by placing a mandrel into the balloon, wrapping a thread around the balloon in the regions where the ribs are desired to be located, and then dipping the balloon, mandrel and thread assembly in a reservoir of elastomeric material, such as silicon, to form an outer ribbed elastomeric coating for the balloon.

The decoupling mechanism of the embodiment illustrated in FIGS. 9–11 also preferably includes a mandrel 54 which extends from outside sidearm 8B through catheter 12 via the interior lumen of pusher 26 and into balloon 40'. Mandrel 52 facilitates inserting balloon 40' within coil 28 and preferably is sized to force the outer wall of the balloon against the inner circumferential surface of coil 28 to enhance the interlocking connection between the coil and balloon.

In operation, the pusher and the mandrel are advanced through catheter 4 until coil 28 is positioned at the desired location (FIG. 9). The mandrel is then retracted or withdrawn from the balloon and the syringe actuated to inflate the balloon 40' as described above (FIG. 10). In this case, it is important that mandrel 54 is sized so that when placed in the pusher lumen, sufficient space between the mandrel and the inner surface of the proximal and distal sections 32, 34 of pusher 26 is formed. In this manner, the interior of balloon 40' can be fluidly coupled to the syringe 6 when stopcock 22 is in the open position and the mandrel is in the pusher. As the balloon inflates and stretches, the ribs generally flatten and the proximal end of coil 28 slides off the distal end portion of balloon 40'. In order to avoid axial displacement of the coil, the balloon can be retracted as it is inflated. Alternatively, the end of the balloon can be positioned where the proximal end of the coil is desired to be finally located. As the balloon inflates, the proximal end of the coil will ultimately be located at the distal end of the balloon. The balloon position can be determined by conventional means such as radiographic techniques. The pusher can then be retracted as shown in FIG. 11 and the balloon deflated. The procedure is repeated if the delivery of additional coils is desired.

Referring to FIGS. 12–15, further embodiments of the invention are shown in which the release or decoupling mechanism comprises a mechanically expandable or locking member rather than a fluidly inflatable/expandable balloon. The expandable locking member fits within the proximal end of the coil and is radially expanded to grip the inner circumferential surface of the coil. When the expandable member is returned to a generally relaxed state so that its diameter decreases, the coil is released.

Figure 12:
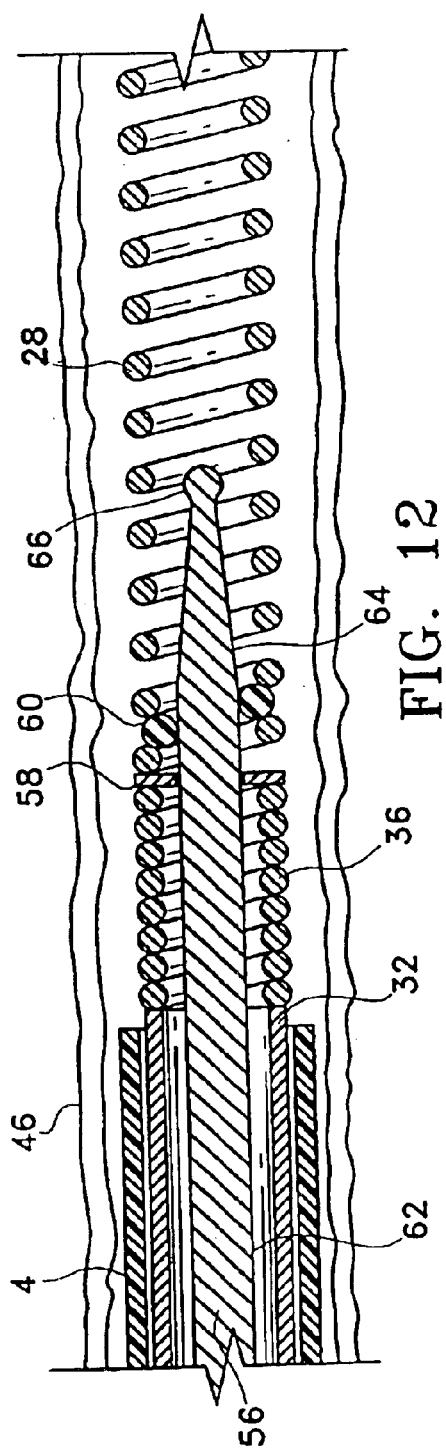
FIG. 12 is an enlarged, fragmentary view of yet another embodiment of the release mechanism of the present invention showing the mechanism in a locked state.
Figure 13:
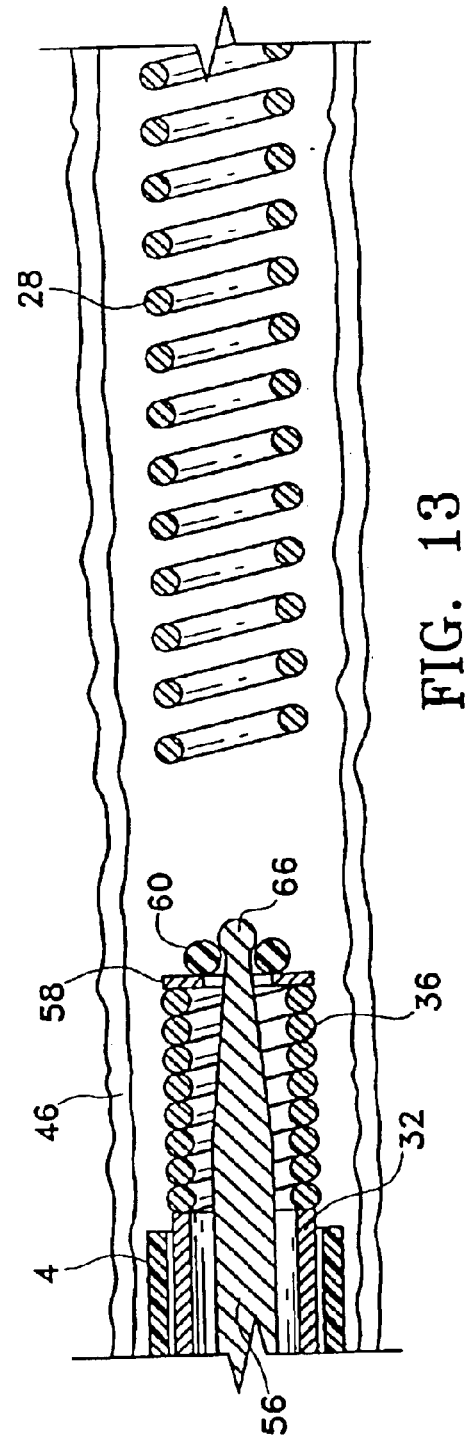
FIG. 13 is a further view of the release mechanism of FIG. 12 illustrating the mechanism in an unlocked configuration.

The decoupling mechanism shown in FIGS. 12 and 13 generally comprises core wire or actuating member 56 and an elastomeric ring or locking member 60, such as an O-ring, which is slidably mounted on core wire 56. Core wire or mandrel 56 includes a proximal locking portion 62, which preferably has a generally uniform diameter, and a distal tapered or unlocking portion. More specifically, the diameter of the core wire locking portion exceeds the inner diameter of the ring such that when the ring is positioned on the locking portion it expands against the inner circumferential surface of coil 28 and frictionally locks the coil thereto (FIG. 12). On the other hand, the tapered portion tapers to a diameter that allows the ring to radially contract and release the coil. In the preferred embodiment, the tapered portion tapers to a diameter that is less than or equal to the inner diameter of the ring when the ring is in its relaxed state. When the core wire is retracted, the tapered portion becomes positioned within the ring and allows the ring to radially contract and release the coil as it returns to its relaxed state (FIG. 13). Core wire 56 can be ground to the desired shape as is conventional in the art.

In addition, the distal portion of actuating member 56 includes a stop member 66 to ensure that the elastomeric ring 60 does not become detached from the actuating member. Otherwise the ring would become free to migrate in the blood stream, which could result in an embolism. A disc 58 optionally may be secured to the distal end of coil 36 by welding, soldering, brazing or adhesive to simplify retraction of the pusher as will be discussed in more detail below.

In operation, ring 60 is positioned on the locking portion of core wire 56 between the core wire and coil 28. Then, the pusher and core wire are both advanced through catheter 4 so that coil 28 eventually extends beyond the catheter and is positioned at the desired location (FIG. 12). Once coil 28 is so positioned, core wire 56 is slowly retracted, causing the tapered distal portion 54 to slide within the opening of ring 60, thereby allowing the ring to return to its relaxed, unexpanded state. In this state, the ring diameter is significantly less than the inner diameter of coil 28 to facilitate rapid coil release. As the core wire is further retracted, stop member 66, which has a larger diameter than the inner diameter of ring 60, catches the ring and carries it as the core wire is completely withdrawn from coil 28 (FIG. 13). When disc 58 is incorporated, the entire pusher 26 can be withdrawn by merely retracting actuating member 56 as stop member 66 acts on coil 36 through ring 60 and disc 58 as is apparent from the drawings.

Figure 14:
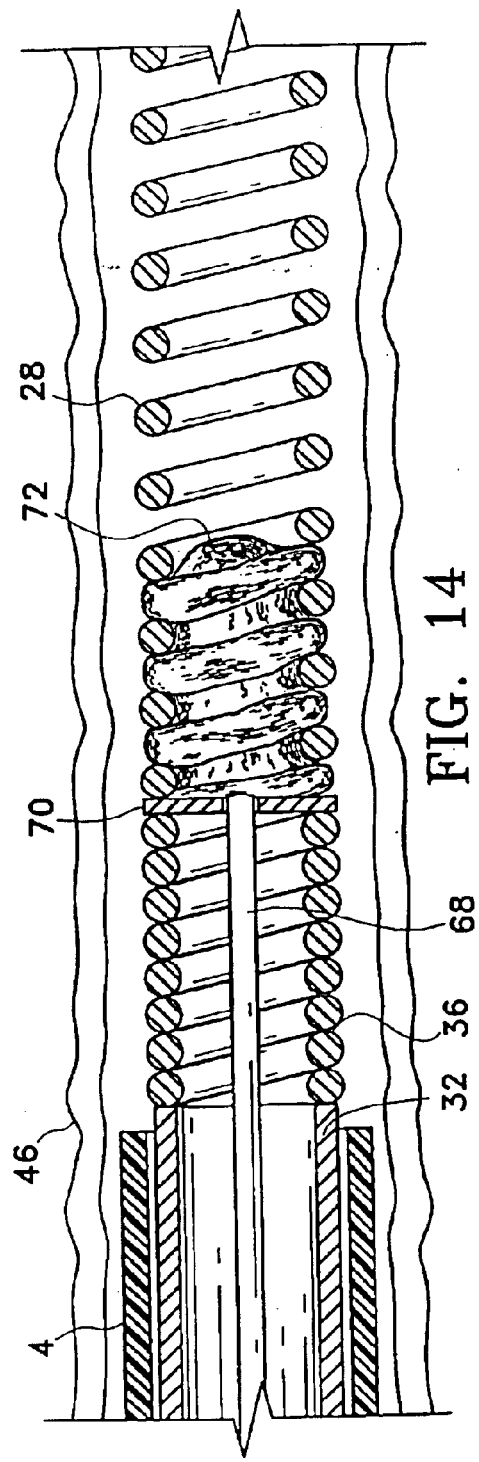
FIG. 14 is yet a further embodiment of the release mechanism of the present invention illustrating the mechanism in a locked configuration.
Figure 15:
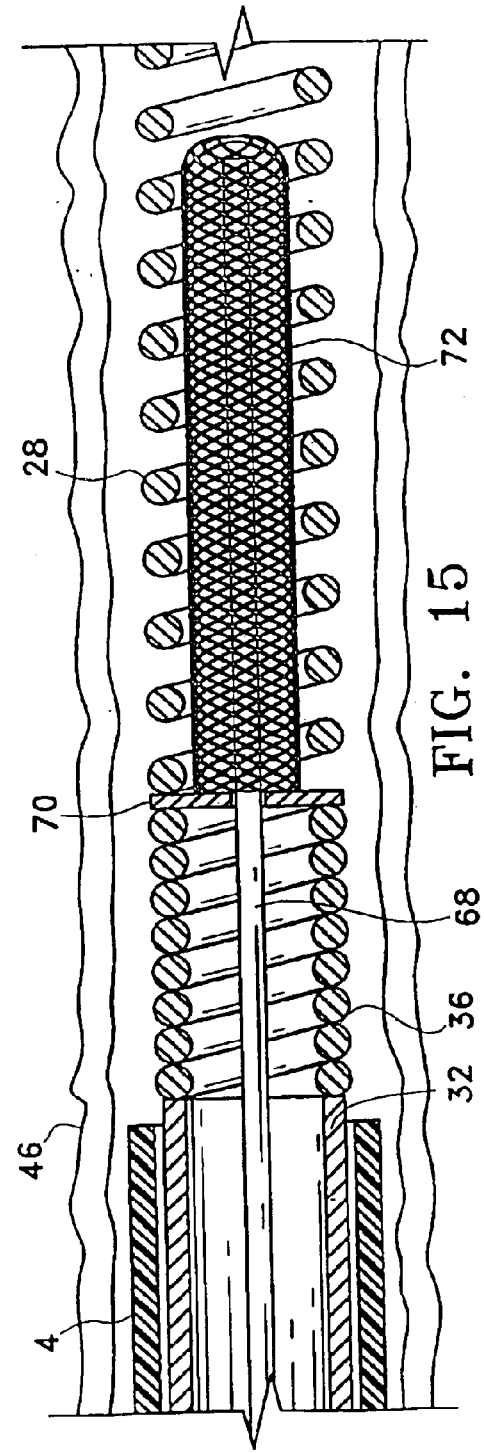
FIG. 15 is a further view of the release mechanism of FIG. 14 showing the mechanism in an unlocked configuration and the implant released therefrom.

Referring to FIGS. 14 and 15, a further embodiment of the release or decoupling mechanism is shown. The decoupling mechanism illustrated in these figures generally comprises a core wire or actuating member 68, disc or retaining member 70 and sleeve or locking member 72. Sleeve 72 is compressed to expand it in the radial direction and interlock the coil to the pusher assembly (FIG. 14). Once in place, it is extended to release the coil therefrom (FIG. 15).

Core wire 68 extends from sidearm 8B as shown in FIG. 1. The distal end portion of core wire 68, preferably is secured to the distal end of sleeve 72 so that when the core wire 68 is retracted, sleeve 72 is compressed in the axial direction against disc 70 as shown in FIG. 14. Sleeve 72 preferably is of a material that, upon compression in the axial direction, will expand radially to interlock with coil 28. Accordingly, sleeve 72 can comprise fabric and, preferably, comprises braided material in which the degree of radial expansion generally depends upon the pitch of the braiding.

The actuator is initially positioned as shown in FIG. 14 with the open end of sleeve 72 compressed against disc 70. The coil is released from the pusher assembly by simply advancing the core wire 68 as shown in FIG. 15 while maintaining pusher 26 is a fixed position. Then, pusher 26 and core wire 68 are concurrently retracted so as to maintain sleeve 72 in its extended position, while withdrawing sleeve 72 from coil 28 without placing any significant mechanical force on the coil in either the radial or axial direction.

The above is a detailed description of several embodiments of the invention. It is recognized that departures from the disclosed embodiments may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A method for detaching an occlusive coil at a site to be occluded in a body, comprising:
    i) providing a catheter having a distal end and an occlusive coil attached to the distal end such that a distal end of the coil is distal to the catheter distal end;
    ii) inserting the catheter in a body such that the coil is placed at a site to be occluded;
    iii) directing a fluid to the catheter distal end through a lumen in said catheter such that the fluid radially expands the catheter distal end to thereby release said coil from the distal end of the catheter.

2. The method of claim 1, wherein said catheter is a tube.

3. The method of claim 1, wherein the catheter distal end further comprises a radially expanding coupling that releases the coil when the coupling is radially expanded by fluid pressure.

4. The method of claim 1, wherein the coil is not in fluid communication with the lumen.

5. A system for delivering an occlusive coil to a vascular passage, comprising:
    an occlusive coil having a distal end; and
    a delivery member having a coupling portion, the coupling portion having a distal end that is proximal to the distal end of the occlusive coil, the coupling portion changing configuration in response to fluid pressure applied to the coupling portion to release the occlusive coil from the coupling portion.

6. The system of claim 5, wherein the coupling portion changes configuration by expanding in a substantially radial direction in response to fluid pressure applied to the coupling portion.

7. The system of claim 5, wherein the coupling portion comprises a coupling member that couples to the occlusive coil by clamping the occlusive coil in a substantially fixed position, the coupling member changing configuration by expanding in a substantially radial direction in response to fluid pressure applied to the coupling member.

8. The system of claim 7, wherein the coupling member comprises a plurality of slots that engage the implant.

9. The system of claim 5, wherein the coupling portion is configured so that the occlusive coil is not in fluid communication with the coupling portion.

10. The system of claim 5, wherein the coupling portion comprises a distal portion of the delivery member.

11. A system for delivering an occlusive coil to a vascular passage, comprising:
    an occlusive coil having a distal end; and
    a delivery member, the delivering member comprising a deformable coupling portion that changes shape in response to fluid pressure applied to the coupling portion to release the occlusive coil from the coupling portion, the coupling portion having a distal end that is proximal to the distal end of the occlusive coil.

12. The system of claim 11, wherein the coupling portion changes shape by expanding substantially radially outward in response to fluid pressure applied to the coupling portion.

13. The system of claim 11, wherein the coupling portion comprises a coupling member that, when in one shape, is configured to couple the occlusive coil to the coupling member.

14. The system of claim 13, wherein the coupling member couples the occlusive coil by clamping action.

15. The system of claim 11, wherein the coupling portion is configured so that the occlusive coil is not in fluid communication with the coupling portion.

16. The system of claim 11, wherein the coupling portion comprises a distal portion of the delivery member.

* * * * *